United States Patent [19]

Matsumura

[11] Patent Number: 4,699,481

[45] Date of Patent: Oct. 13, 1987

[54] STEREOSCOPIC MICROSCOPE

[75] Inventor: Isao Matsumura, Yokosuka, Japan

[73] Assignee: Canon Kabushiki Kaisha, Tokyo, Japan

[21] Appl. No.: 767,869

[22] Filed: Aug. 21, 1985

[30] Foreign Application Priority Data

Sep. 1, 1984 [JP] Japan .................................. 59-183045
Jan. 31, 1985 [JP] Japan .................................. 60-17051

[51] Int. Cl.$^4$ ........................... A61B 3/10; A61B 3/14
[52] U.S. Cl. ..................................... 351/205; 351/206
[58] Field of Search ................ 351/205, 206, 212, 247

[56] References Cited

U.S. PATENT DOCUMENTS 4,569,576  2/1986  Karpov .............................. 351/247

Primary Examiner—Rodney B. Bovernick
Attorney, Agent, or Firm—Fitzpatrick, Cella, Harper & Scinto

[57] ABSTRACT

A stereoscopic microscope comprises a first index to be projected to a cornea of an eye under inspection, a pair of observation optical systems for observing a reflected image from the cornea to which the first index is projected, and a second reference index to be observed by the observation optical systems.

11 Claims, 7 Drawing Figures

4,699,481

STEREOSCOPIC MICROSCOPE

BACKGROUND OF THE INVENTION

1. Field of the Invention

The present invention relates to a stereoscopic microscope having a mechanism to allow identification of a shape of a cornea of an eye under inspection, suitable for use in an ophthalmologic operation,

2. Description of the Prior Art

A stereoscopic microscope has been widely used in the medical field such as for an operation or as a diagnostic tool, the research field and the industrial field, and is useful for enhancement of precision and safety of an operation. For example, when an eye, which is a precise optical system is diseased, appropriate measures recover its function is taken. When an operation is made for an eyeball, it is an important mission to recover the shape and the function thereof. In an operation for a cataract, it is an important factor for determining the success of the operation to recover the shape of the cornea by the operation. Accordingly, it is very effective to add a function of measuring the shape of the cornea to an operation microscope to allow measurement and display of the shapes of the cornea before and after the operation.

The prior art ophthalmologic operation microscope has only a function to project the eye under inspection has cannot allow the observation of the shape of the recovered cornea during the operation.

The optical system of the stereoscopic microscope is classied into three types, a fixed magnification type, a drum variable magnification type and a zoom variable magnification type.

The zoom variable magnification type preferably is used for the operation, because different magnifications are required in different stages of the operation.

However, when the magnification is changed during the operation, the measurement of the shape of the cornea varies with the magnification. As the measurement varies in spite of the fact that the same object is observed, there is confusion in analyzing the measurements. As a result, in the prior art microscope, a characteristic of the zoom variable magnification is not fully utilized.

SUMMARY OF THE INVENTION

It is an object of the present invention to provide a stereoscopic microscope which allow precise observation of a shape of a cornea during an ophthalmologic operation.

It is another object of the present invention to provide a stereoscopic microscope which compensates for a variation of measurement due to change of magnification so that a characteristic of variable magnification is fully utilized.

DESCRIPTION OF THE PREFERRED EMBODIMENTS

Figures 1, 2:
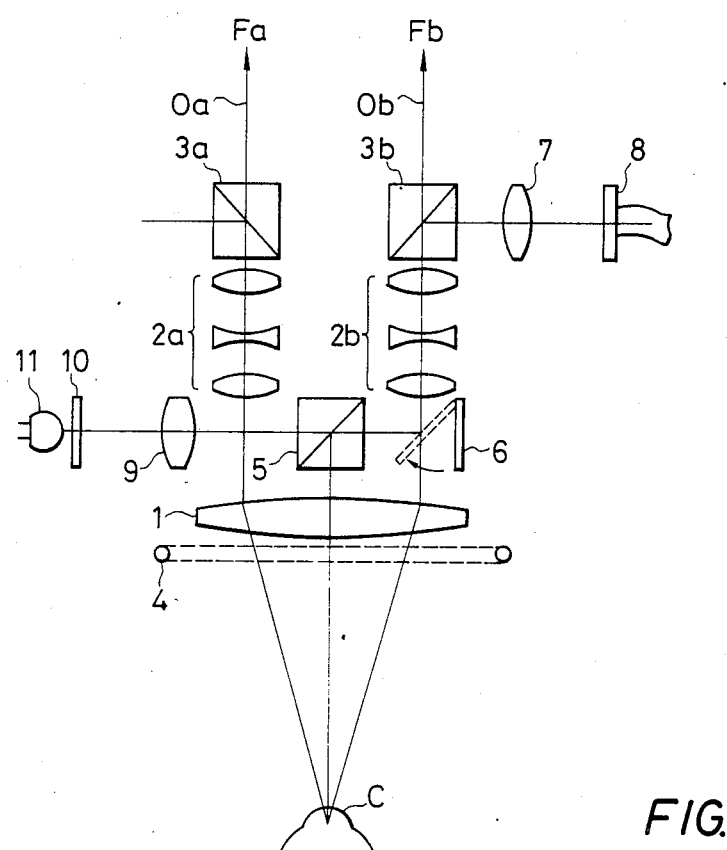
FIG. 1 shows embodiment of the present invention.
FIG. 2 is a front view of an index plate.

FIG. 1 shows an optical system used to observe an eye E under inspection and FIG. 2 is a front view of an index plate having a ring index. In FIG. 1, the eye E under inspection is steroscopically observed by an inspector through a common object lens 1 arranged in front of the eye E, a pair of zoom variable magnification systems 2a and 2b arranged along left and right optical axes 0a and 0b, respectively, beam splitters 3a and 3b and finder optical systems Fa and Fb, respectively.

A ring-shaped light source 4 is arranged between the eye E and the object lens 1 as a part of a cornea shape measuring optical system, a beam splitter 5 is arranged on an optical axis of the object lens 1 behind the object lens 1 and a rotatable mirror 6 is retractably arranged on the optical axis 0b. A photosensing plane 8 consisting of a focusing lens 7 and a two-dimensional charge coupled device (CDD) is arranged on a reflection side of the beam splitter 3b so that it senses a light flux reflected by the rotatable mirror 6 through the zoom variable magnification system 2b and the beam splitter 3b of the stereoscopic observation optical system.

A relay lens 9, a reference ring-shaped index plate 10 shown in FIG. 2 and a light source 11 are arranged on the opposite side of the beam splitter 5 to the rotatable mirror 6 to form a variable magnification correction optical system.

In present embodiment, the light flux emanated from the eye E is changed to an afocal light flux by the object lens 1 and it impinges to the zoom variable magnification system 2a. Then, it is applied to the beam splitter 3a and a portion of the light flux is used for monitoring or a TV camera and the remainder is directed to an eye of an inspector. Similarly, the light flux impinged to the zoom variable magnification system 2b through the object lens 1 is directed to an eye of the inspector through the beam splitter 3b and the finder optical system Fb. In this manner, the light flux through the finder optical system Fa and the light flux through the finder optical sytem Fb presents a stereoscopic image to the eyes of the inspector.

On the other hand, the light flux from the ring-shaped light source 4 forms a Myer image which is a ring-shaped reflection image of the cornea on the cornea C of the eye E under inspection. The Myer image is directed to the zoom variable magnification system 2b through the object lens 1, beam splitter 5 and the rotatable mirror 6 inserted in the optical path 0b, laterally reflected by the beam splitter 3b and projected onto the photo-sensing device plane 8 by the focusing lens 7 so that a distortion of the cornea C is numerically measured. A portion of the light flux is observed by the inspector through the finder optical systerm Fb.

The reference index plate 10 shown in FIG. 2 is illuminated by the light source 11 and a light flux from a ring slit-shaped index 10p formed on the index plate 10 is converted to an afocal light flux by the relay lens 9, passes through the beam splitter 5 without deflection, is directed to the zoom variable magnification system 2b through the rotatable mirror 6, is reflected by the beam splitter 3b and is focused onto the photo-sensing device plane 8 by the focusing lens 7. The size of the reflection image of the cornea is numerated with respect to the image of the index 10p.

In order to observe and measure the shape of the cornea through the optical system, the inspector aligns the reflection image of the cornea of the ring-shaped light source 4 to the index 10p. The focus adjustment in a direction of an optical axis is done by the finder optical systems Fa and Fb. After the adjustment, a correction factor of a projection magnification by the lens optical system including the zoom variable magnification system 2b is determined based on the size of the ring shaped index 10p focused on the photosensing device plane 8. Then, the size and shape of the reflection image of the cornea of the ring-shaped light source 4 are measured on the photo-sensing device plane 8 and the shape of the cornea is determined based on the correction factor.

In accordance with the present invention, the cornea C can be observed and measured with a high precision by providing the magnification correction means which uses the reference index. Higher precesion measurement is attained by adding means for restricting the size of the reflection image of the cornea as shown in FIG. 3.

Figure 3:
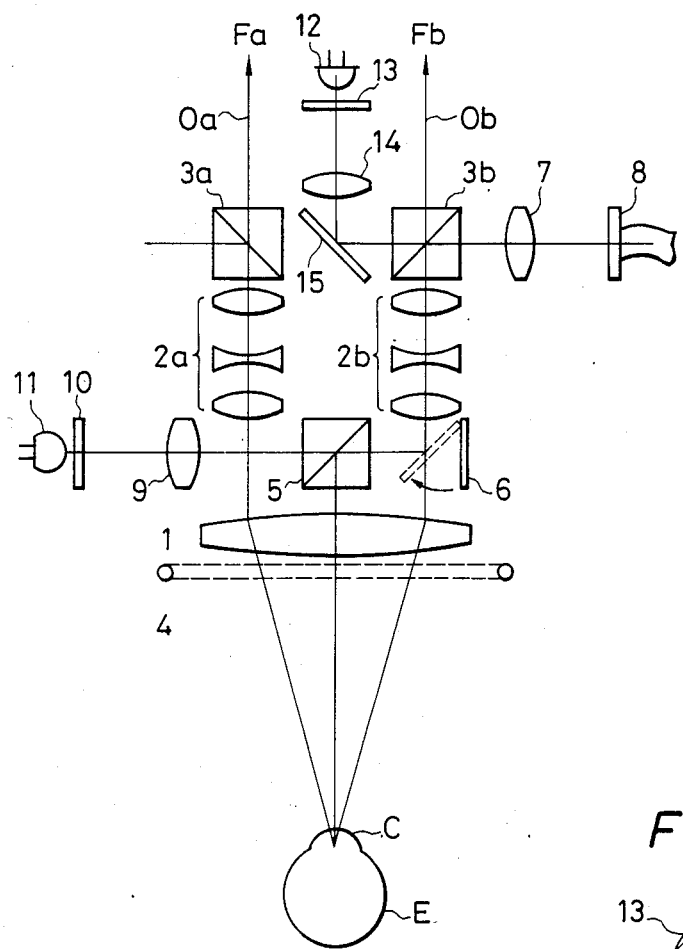
FIG. 3 shows an optical system of a second embodiment.
Figure 4:
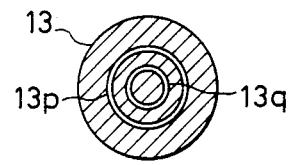
FIG. 4 is a front view of an index plate.

In an embodiment shown in FIG. 3, an image from an optical system which includes, in addition to the elements shown in FIG. 1, a light source 12, an index plate 13 having dual-ring slit-shaped indices 13p and 13q, a relay lens 14 and a mirror 15 is directed to the photo-sensing device plane 8 through the beam splitter 3b.

A light flux emanated from the indices 13p and 13q on the index plate 13 illuminated by the light source 12 is projected onto the photo-sensing device plane 8 through the relay lens 14, mirror 15, beam splitter 3b and the imaging lens 7 without routing the zoom variable magnification system. By adjusting the zoom vairable magnification systems 2a and 2b to bring the image of the ring-shaped light source 4 between the indices 13p and 13q focused on the photo-sensing device plane 8, the size of the reflection image of the cornea of the ring-shaped light source 4 can be maintained substantially constant. Obstacle to the observation or measurement due to an improper size of an observation view field by the finder optical systems Fa and Fb or an improper size of the reflection image of the cornea on the photo-sensing device plane 8 is prevented and the observation and measurement at a proper position are allowed.

Figure 5:
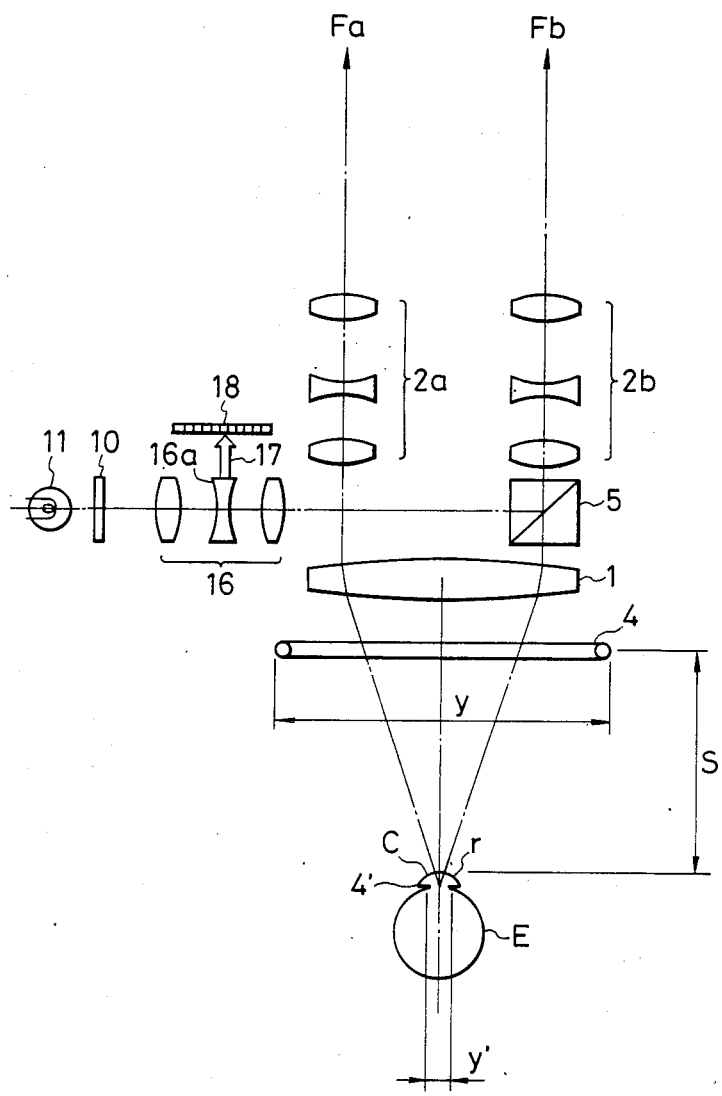
FIG. 5 shows an optical arrangement of a third embodiment.

FIG. 5 shows a third embodiment of the present invention. A light flux from an eye E under inspection illuminated by an illumination optical system (no shown) passes through an object lens 1 and a zoom variable magnification system 2a and is observed through a finder optical system Fa. On the other hand, it passes through a beam splitter 5 and a zoom variable magnification system 2b and is observed through a finder optical system Fb. A stereoscopic image is observed through the two finder optical systems Fa and Fb.

A light from a ring-shaped light source 4 forms a virtual image 4' which is a reflection image of a cornea C of the eye E under inspection and the virtual image 4' is observed by the finder optical systems Fa and Fb through the object lens 1 and the zoom variable magnification systems 2a and 2b.

The index plate 10 having the reference ring-shaped index 10p is illuminated by a light source 11 and observed by the finder optical system Fb through a zoom lens 16, the beam splitter 5 and the zoom variable magnification system 2b.

Let us consider the sizes of the ring-shaped light source 4 and the reflection image 4' of the cornea A diameter y of the ring-shaped light source 4, a distance s between the ring-shaped light source 4 and the cornea c, a radius $\gamma$ of curvature of the cornea c and a diameter y' of the reflection image of the ring-shaped light source 4 by the cornea have a relationship of $\gamma = 2sy'/y - y'$. Thus, $\gamma$ is determined by measuring y'.

A pointing needle 17 is mounted on a variator 16a in the zoom lens 16 in addition to the ring-shaped index 10p to allow qualitative and quantitative check of the shape of the cornea before, during and after the ophthalmologic operation. Thus, a scale representing the radius $\gamma$ of curvature of the cornea is read by an encoder 18.

The zoom lens 16 is used to variably magnify the image of the ring-shaped index 10p.

By setting the radius of curvature of the cornea to be recovered by the operation for each patient eye, that is, if the position of the pointing needle 17 is fixed, the operation operates the ophthalmologic operation while the image of the ring-shaped index 10p at the pointed position is overlapped on the reflection image of the cornea.

Figure 6:
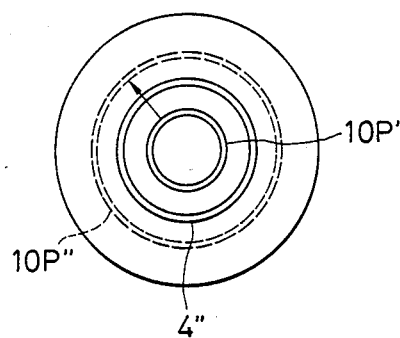
FIG. 6 shows a reflected image of a ring index reflected by a cornea and a ring-shaped index image as viewed by an eye-piece.

It may be used differently as shown below. If the reflection image of the cornea deviates from an anticipated real circle where the cornea is to be recovered such that the reflection image of the cornea is the real circle having a predetermined diameter, for example, if the shape is elliptic, the variator 16a is moved to vary the magnification for the reference ring-shaped index 10p to qualitatively detect the deviation from the real circle. Absolute values of major diameter and a minor diameter of the ellipse and absolute values of the radii of curvature of the cornea in the major and minor diameter directions are quantatively detected based on the position of the pointing needle 17 on the encoder 18. FIG. 6 shows that the reference ring-shaped index moves from 10p' to 10p" as the variator 16a moves, relative to the reflection image 4" of the cornea observed by the finder optical system.

Figure 7:
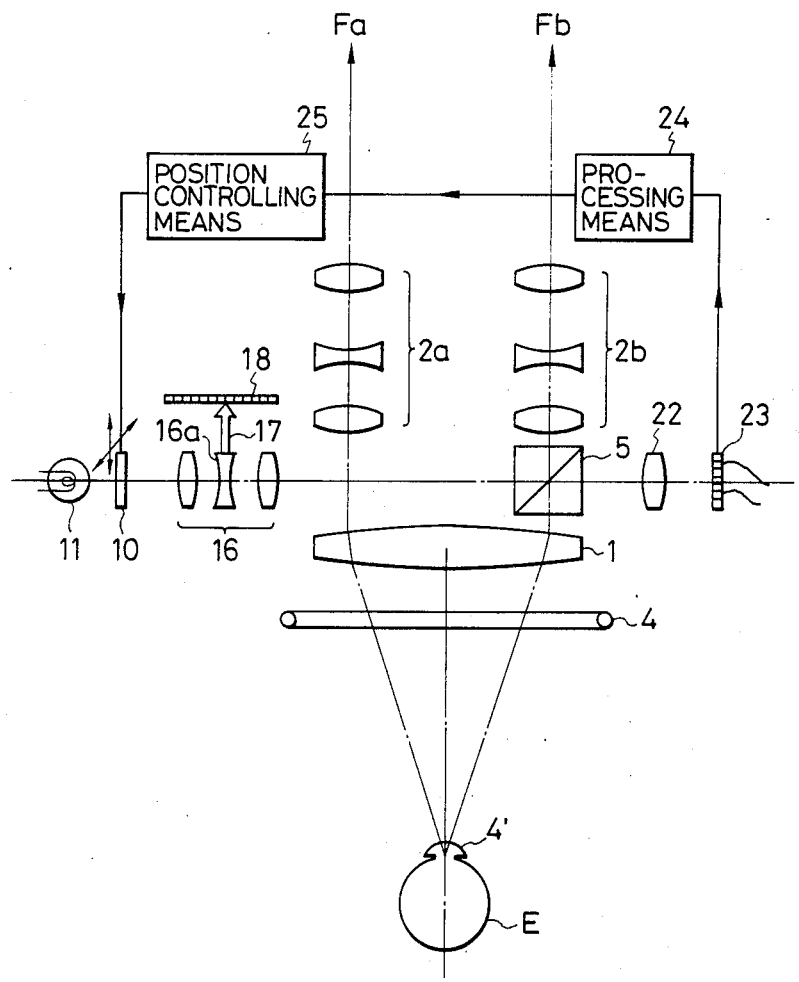
FIG. 7 shows a fourth embodiment.

FIG. 7 shows a fourth embodiment. The observation optical system of the present embodiment is identical to that of the embodiment of FIG. 5. In FIG. 7, a reflection image 4' of the cornea of the ring-shaped light source 4 is projected onto a two-dimension solidstate imaging device 23 through an object lens 1, a beam splitter 5 and a relay lens 22. On the other hand, the ring-shaped index 10p on the index plate 10 is focused onto the solid-state imaging device 23 through the zoom lens 16, beam splitter 5 and relay lens 22. A deviation between the two index images can be calculated by processing means 24 based on coordinates of the images on the solid-state imaging device 23. The position of the index plate 10 is controlled by position control means 25 in accordance with the output of the processing means 24 so that the image of the ring-shaped index 10p is aligned to the reflection image 4' of the ring-shaped light source 4 to facilitate the comparison of the two images.

The deviation between the two index images may be qualitatively observed by the finder optical system Fb.

By the provision of the solid-state imaging device 23, the deviations of the reflection image 4" of the cornea in FIG. 6 from the ring-shaped index images 10p' and 10p" in the diameter directions can be quantatively detected and thus, the shape of the cornea can be quantatively detected.

In the above embodiment, the distance S between the ring-shaped light source 4 and the eye E under inspection is fixed. Alternatively, the distance S may be varied, that is, the ring-shaped light source 4 may be displaced relative to the fixed eye E so that the shape of the cornea is observed at a region different from a near-region or far-region of an eye axis on the cornea. It is preferable to move the variator 16a with the movement of the ring-shpaed light source 4 to correct the magnification for the reference index.

It is preferable to turn on and off the light source 11 which illuminates the reference index plate, as required or insert a light flux interrupt means in the light path so that the first index and the second reference index projected to the cornea of the eye under inspection are selectively presented.

In the above description, the object under inspection is an eyeball, but the object is not limited to an eyeball but may be any article which forms a reflection image when illuminated by a light source. The present invention is applicable to not only the medical field for such as use for operations but also various research fields and industrial fields.

What is claimed is:

1. A stereoscopic microscope provided with a pair of variable magnification optical systems, comprising:
    a first index projected onto a cornea to be examined;
    a measurement system for measuring, by means of image pick-up means through at least one of said paired variable magnification optical systems, a reflection image reflected at the cornea when said first index is projected onto the cornea of the eye to be examined; and
    a second index positions for being measured by said measurement system without use of a reflected image thereof so as to measure the magnification of said variable magnification optical system and then correct said measured value of said cornea reflection image by said image pick-up means.

2. A stereoscopic microscope according to claim 1, comprising a common object lens.

3. A stereoscopic microscope according to claim 1 wherein said first and second indices are of ring shape.

4. A stereoscopic microscope according to claim 1, comprising an optical system for directing toward said image pick-up means not through said variable magnification optical systems a reference index different from said second index.

5. A stereoscopic microscope according to claim 4 wherein said reference index other than said second index has two ring-shaped indices of different diameters.

6. A stereoscopic microscope according to claim 1 wherein said second index is movable normally to an optical axis.

7. A stereoscopic microscope according to claim 1, futher comprising another variable magnification optical system for varying a magnification of image of said second index.

8. A stereo microscope according to claim 7 wherein said first index is movable toward the eye under inspection and a magnification of said variable magnification optical system is selected in accordance with a position of said first index.

9. A stereoscopic microscopic according to claim 1 wherein at least one of said first and second indices is selectively presented.

10. A stereoscopic microscope provided with pair of variable magnification optical systems, comprising:
    a first index projected onto a cornea to be examined;
    a measurement systems for measuring, by means of image pick-up means through at least one of said paired variable magnification optical systems, a reflection image reflected at the cornea when said first index is projected onto the cornea of the eye to be examined;
    a second index positioned for being measured by said measurement system without use of a reflected image thereof so as to measure the magnification of said variable magnification optical systems and then correct said measured value of said cornea reflection image by said image pick-up means; and
    optical path selecting means for selecting either one of optical paths for directing the light from said second index toward said variable magnification optical systems and for directing the cornea reflection image of said first index toward said variable magnification optical systems.

11. An ophthalmologic microscope comprising:
    a first index projected onto a cornea to be examined;
    a measurement system for measuring, by means of image pick-up means through a determined variable magnification optical system, a reflection image reflected at the cornea when said first index is projected onto the cornea of the eye to be examined; and
    a second index positioned for being measured by said measurement system without use of a reflected image thereof so as to measure the value of the magnification of said variable magnification optical system and then correct said measured value of said cornea reflection image by said image pick-up means.

* * * * *

UNITED STATES PATENT AND TRADEMARK OFFICE
CERTIFICATE OF CORRECTION

PATENT NO. : 4,699,481         Page 1 of 3

DATED      : October 13, 1987

INVENTOR(S): ISAO MATSUMURA

It is certified that error appears in the above-identified patent and that said Letters Patent is hereby corrected as shown below:

[56] REFERENCES CITED, U.S. PATENT DOCUMENTS
    "Karpov" should read --Karpov, et al.

COLUMN 1
    Line 10, "operation," should read --operation.--.
    Line 11, "Descripition" should read --Description--.
    Line 18, "recover" should read --to recover--; "is taken." should read --are to be taken--.
    Line 30, "has cannot" should read --and cannot--.
    Line 33, "classied" should read --classified--.
    Lines 35-36, "type.¶The" should read --type. The--.
    Line 37, "the" should read --an--.
    Line 51, "allow" should read --allows--.
    Line 61, "embodiment" should read --a first embodiment--.

COLUMN 2
    Line 59, "systerm" should read --system--.

COLUMN 3
    Line 21, "precesion" should read --precision--.
    Line 36, "vaira-" should read --varia--.
    Line 51, "(no" should read --(not--.

UNITED STATES PATENT AND TRADEMARK OFFICE
CERTIFICATE OF CORRECTION

PATENT NO. : 4,699,481

DATED : October 13, 1987

INVENTOR(S) : ISAO MATSUMURA

It is certified that error appears in the above-identified patent and that said Letters Patent is hereby corrected as shown below:

COLUMN 4
    Line 7, "cornea c," should read --cornea C,--; "cornea c," should read --cornea C--.
    Line 38, "quantatively" should read --quantitatively--; "solidstate" should read --solid-state--.
    Line 68, "quantatively" should read --quantitatively--.

COLUMN 5
    Line 1, "quantatively" should read --quantitatively--.
    Line 11, "ring-shpaed" should read --ring-shaped--.
    Line 25, "as use" should read --use as--.
    Line 37, change "positions" to --positioned--.
    Line 40, "system" should read --systems--.

COLUMN 6
    Line 10, "stereo" should read --stereoscopic--.
    Line 15, "microscopic" should read --microscope--.

UNITED STATES PATENT AND TRADEMARK OFFICE
CERTIFICATE OF CORRECTION

PATENT NO. : 4,699,481

DATED : October 13, 1987

INVENTOR(S) : Isao Matsumura

It is certified that error appears in the above-identified patent and that said Letters Patent is hereby corrected as shown below:

Line 18, "pair" should read -- a pair --.
Line 21, "systems" should read -- system --.

Signed and Sealed this

Twenty-seventh Day of September, 1988

Attest:

DONALD J. QUIGG

*Attesting Officer*  *Commissioner of Patents and Trademarks*